United States Patent [19]

Nolf et al.

[11] Patent Number: 5,450,192

[45] Date of Patent: Sep. 12, 1995

[54] APPARATUS INCLUDING AN INDEX CONTINUITY CELL FOR MEASURING THE INDEX PROFILE OF AN OPTICAL FIBER PREFORM HAVING AN OUTER ENVELOPE AND A CORE

[75] Inventors: Michel Nolf, Laroche; Patrick Chollet, Lannion; Paul Fossey, Tregastel, all of France

[73] Assignee: France Telecom, Paris, France

[21] Appl. No.: 172,087

[22] Filed: Dec. 22, 1993

[30] Foreign Application Priority Data

Dec. 24, 1992 [FR] France ............ 92 15731

[51] Int. Cl.$^6$ ............ G01N 21/41; G01N 21/88
[52] U.S. Cl. ............ 356/73.1; 356/244
[58] Field of Search ............ 356/73.1, 244

[56] References Cited

U.S. PATENT DOCUMENTS 5,220,403 6/1993 Batchelder et al. ............ 356/349 X

FOREIGN PATENT DOCUMENTS

WO91/17425 11/1991 WIPO .

Primary Examiner—Vincent P. McGraw
Attorney, Agent, or Firm—Blakely, Sokoloff, Taylor & Zafman

[57] ABSTRACT

The invention relates to apparatus for measuring the index profile of an optical fiber preform that includes an outer envelope and a core. According to the invention, a deformable and transparent separation interface is provided between a deformable index isotropy medium and the outside surface of the envelope of the preform, said deformable separation interface adapting the deformable index isotropy medium to the outside surface of the envelope of the preform at least over an annular zone thereof, which zone corresponds to an optical measurement zone situated on the path of a light beam, said deformable and transparent interface, and inlet and outlet optical surfaces for the light beam all having an index close to the index of said medium.

38 Claims, 6 Drawing Sheets

FIG.1

FIG_2

FIG.3

FIG_4

$u = k \tan (\text{dev})$

FIG. 5

$\dfrac{u_2 - u_1}{d_2 - d_1} = k \tan(\text{dev})$

FIG. 6

* A Analog
* D Digital
* B Binary

FIG_7

APPARATUS INCLUDING AN INDEX CONTINUITY CELL FOR MEASURING THE INDEX PROFILE OF AN OPTICAL FIBER PREFORM HAVING AN OUTER ENVELOPE AND A CORE

The present invention relates to apparatus for determining the index profile of an optical fiber preform.

BACKGROUND OF THE INVENTION

In the technical field of optical fiber preforms, there are certain constraints that it is essential to satisfy. Preforms are now being made with greater and greater diameters, e.g. by the following manufacturing methods: plasma outside inside deposition (POID), furnace chemical vapor deposition (FCVD), and vapor axial deposition (VAD). Certain applications require preforms to be made having a core index that is very high (of the order of $50 \times 10^{-3}$; e.g. for manufacturing optical amplification fibers.

The constraint relating to the (refractive) index of the core of a preform applies to laser amplifiers, whereas the constraint relating to the diameter of a preform applies to the fiber-drawing capacity thereof, i.e. to the length of fiber that can be obtained in a single piece from a given preform, which capacity is at present of the order of 200 km and is likely to be considerably increased in a relatively near future given the necessity of reducing the number of splices in undersea cables between two repeaters, for example.

The only measuring apparatus of the type mentioned above that is available on the market and that is capable of satisfying the needs of users, at least in part, is covered by several patents, such as EP-A2-0377818, WO90/05904, and WO-91/17425. Unfortunately, that known apparatus suffers from several drawbacks, in particular with respect to:

1) price, which is very high and which is not within the reach of most laboratories in which may need to determine the index profile of an optical fiber preform;
2) the method of use, which requires the preform to be driven with motion relative to the measurement cell, which can have the consequence of the preform being damaged due to accidental mishandling, thus requiring it to be discarded and replaced by another, with a considerable loss of income when it is understood that the present cost of optical fiber is about 1 franc per meter;
3) the transparent liquid medium used for optical continuity around the preform, i.e. for ensuring index isotropy, comes into direct contact with the preform, thereby giving rise to severe problems of sealing and of cleaning in the event of the liquid leaking, said liquid having the consistency of an oil;
4) preform diameter lies in a relatively restricted range of values, such that a relatively large number of measurement cells need to be used, with each cell accepting only those preforms whose diameters lie within a range between two end values that are extremely close together;
5) the measurable variation in preform index, $\Delta n$, is less than $40 \times 10^{-3}$, whereas there is a requirement to achieve values in the following range:

$$-10^{-2} < \Delta n > +5 \times 10^{-2}$$

6) preform length is limited by size constraints; and
7) the constraints relating to alignment of the preform relative to the measurement cell, which constraints are very severe.

Thus, the technical problem to be solved consists in designing a measurement apparatus of the type mentioned above which satisfies the requirements of the art better than previously known apparatus of the same type seeking to achieve the same aim, and in particular better with respect to the constraints listed above under 1) to 7).

OBJECTS AND SUMMARY OF THE INVENTION

The present invention provides an apparatus for measuring the index profile of an optical fiber preform comprising an outer envelope and a core, the apparatus comprising:

preform support means;

emission means for emitting a light beam that is to scan a cross-section of the preform along a diameter thereof;

an index continuity cell comprising an enclosure provided with a through opening, and serving to press the enclosure around a peripheral annular zone of the preform, together with a cavity formed inside the enclosure so as to surround the above-specified envelope and so as to be in optical communication therewith;

a medium that is deformable and transparent for the light beam being contained inside the cavity of the enclosure and providing optical index continuity, i.e. isotropy, around the preform and relative to the index of the envelope thereof, this being done by passing through a first optical surface constituting an inlet surface for the light beam that scans the preform diametrically, through said medium, and through a second optical surface which constitutes an outlet surface for the light beam, the inlet and outlet first and second optical surfaces being provided in the enclosure transversely relative to the longitudinal axis of the preform, their transverse size being at least equal to the diameter of the preform;

scanning means for diametrically scanning the light beam across the cross-section of the preform along the diameter thereof;

position determining means for determining the position of the incident light beam on the preform relative to the index continuity cell;

receiver and measurement means for receiving the light beam transmitted through the preform, together with deflection, relative to each incidence point of the emitted beam, said receiver and measurement means also serving to measure the deflection of the beam transmitted through the preform relative to each incidence point, and delivering a signal that is a function of said deflection;

means for processing each of the signals delivered by the receiver and measurement means and also for calculating the variation in the index of the preform along a diameter of its cross-section relative to the index of said medium, with this being done on the basis of a set of measurements of deflection;

wherein a deformable and transparent separation interface exists between the deformable index isotropy medium and the outside surface of the envelope of the preform, said interface serving to adapt the deformable index isotropy medium to the outside surface of the envelope of the preform at least over an angular zone thereof, which zone corresponds to an optical measurement zone situated on the path of the light beam, said deformable and transparent interface, and said inlet and outlet optical surfaces for the light beam having a refractive index close to the index of said medium.

In an advantageous disposition of this embodiment, the index isotropy medium is constituted by a liquid or viscous transparent substance, the deformable and transparent interface is constituted by a resilient and impermeable membrane, and the apparatus also includes injection means for injecting the substance into the cavity of the enclosure of the index continuity cell.

The use of such a separation interface that is transparent, elastic, and impermeable between the liquid or viscous index isotropy medium and the outer envelope (or cladding) of the preform makes it possible to eliminate the problem of such a medium leaking, while still enabling the same index continuity cell to be applied to preforms of diameters lying in a relatively wide range.

In a preferred variant of this disposition, the resilient and impermeable membrane is extended from each of its transverse annular edges relative to the longitudinal axis of the preform firstly radially outwardly and secondly longitudinally inwardly from the optical measurement zone so as to define a substantially toroidal fluid-tight continuous chamber designed to be received in the cavity of the enclosure and to be filled with the above-mentioned transparent substance.

This variant makes it possible significantly to improve the sealing of the apparatus relative to the optical isotropy medium, while retaining the same flexibility with respect to adapting the index continuity cell to preforms of different diameters.

In another preferred embodiment, the emission means and the receiver and measurement means, in association with the scanning means for diametrically scanning the cross-section of the preform and also with the above-mentioned calculating and processing means are integrated in a unitary assembly constituting a measurement cell, which is substantially in the form of a horseshoe cell and is designed to co-operate with the enclosure surrounding the preform and containing the index isotropy medium for the purpose of determining the index profile of said preform, the emission means being disposed inside a first arm of the horseshoe-shaped measurement cell while the receiver and measurement means are disposed in the second arm thereof opposite to the first, the first and second arms respectively including a first window for passing the beam emitted by the first arm, and a second window for passing the beam received by the second arm.

In a preferred disposition of the second embodiment specified above, the scanning means for scanning the preform transversely and integrated in the measurement cell comprise:

two relative slide rails between the measurement cell and the index continuity cell, extending transversely relative to the longitudinal axis of the preform;

two transverse guide grooves for the two relative slide rails; and drive means for driving the measurement cell parallel to the inlet and outlet surfaces of the index continuity cell.

In an advantageous implementation of this disposition:

the two relative slide rails between the measurement cell and the index continuity cell are provided on the two inside faces of the two opposite arms of the horseshoe-shaped measurement cell; and the two guide grooves for said two relative slide rails are formed in two sides of the index continuity cell, which sides extend transversely relative to the longitudinal axis of the preform and correspond respectively to the inlet and outlet surfaces for the light beam for transversely scanning the preform, said inlet and outlet surfaces occupying the bottoms of the guide grooves.

Also in accordance with an advantageous variant of this implementation:

the two relative slide rails between the measurement cell and the index continuity cell are provided on two sides of the index continuity cell, which sides extend transversely relative to the longitudinal axis of the preform and correspond to the inlet and outlet surfaces for the light beam for transversely scanning the preform, said inlet and outlet surfaces occupying the radially outermost sides of the two rails; and the two guide grooves for the two relative slide rails are provided in the inside faces of the two opposite arms of the horseshoe-shaped measurement cell.

In another preferred disposition of the second embodiment specified earlier on and applicable to the two above implementations, the drive means for driving the measurement cell comprise a handle formed in the web linking together the two opposite arms of said horseshoe-shaped measurement cell, said handle being designed to enable an operator to cause the measurement cell to slide progressively transversely relative to the longitudinal axis of the preform and parallel to the inlet and outlet surfaces of the index continuity cell, with this being done with the assistance of position determining means for determining the position of the incident light beam on the preform.

In an advantageous variant of this other disposition, the drive means for driving the measurement cell comprise two stepper motors for two driving racks each disposed on the axially outer sides of each relative slide rail, together with housings distributed along the opposite axially inner walls of each transverse guide groove for a corresponding rail and designed to receive the teeth of the corresponding rack as the rack advances.

In accordance with yet another advantageous disposition of the second above-specified embodiment, the measurement cell also has integrated therein display means and/or data input means and/or means for playing back data from the computer interface.

In accordance with the invention, the means for determining the position of the incident light beam on the preform comprise a magnetic strip secured to the index continuity cell in particular by means of adhesive, and preferably in alignment with the transverse dimension of the inlet surface of the beam for performing transverse scanning of the preform; in addition, the index continuity cell co-operates with means for holding said cell in position relative to the measurement zone localized on the preform, and the means for holding the index continuity cell in position comprise two lateral clamping collars disposed on either side of said cell and fitted with respective sealing rings, in particular rings made of elastomer, each received in an annular groove formed in the inside wall of the associated collar, each sealing ring serving to apply clamping force from the corresponding collar to the preform, thereby maintaining the index continuity cell in position relative to said preform.

BRIEF DESCRIPTION OF THE DRAWINGS

Other advantages of the invention will appear on examining the following detailed description and the accompanying drawings, in which.

MORE DETAILED DESCRIPTION

Figure 1:
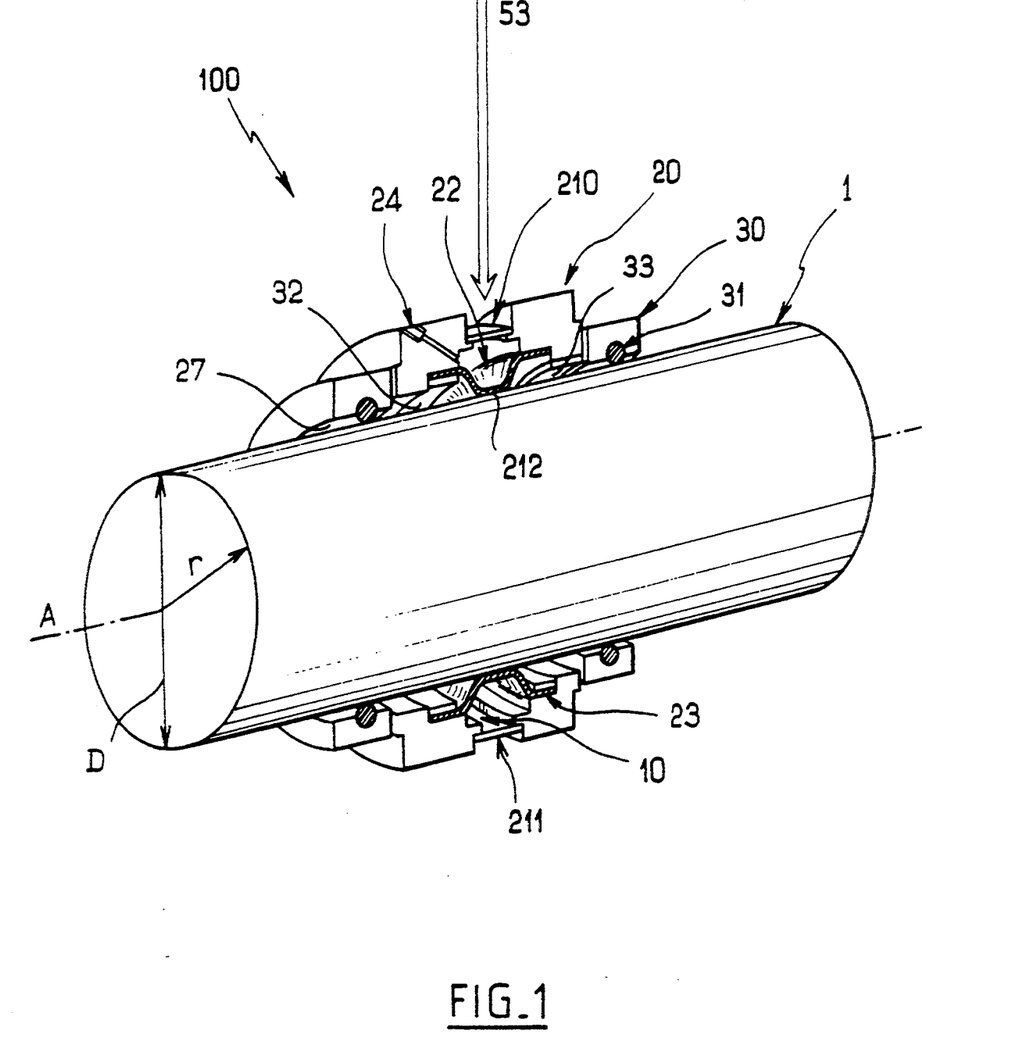
FIG. 1 is a partially cut away diagrammatic perspective view in the axial direction of an embodiment of an optical index continuity cell of the invention.

With reference initially to FIG. 1, there can be seen a diagrammatic perspective view of a cylindrical optical fiber preform 1 whose index profile is to be determined. A substantially toroidal index continuity cell 100 is applied to said preform 1 (which is supported by suitable means that are not shown but may advantageously be constituted by V-supports). An embodiment of the index continuity cell 100 in accordance with the present invention comprises an enclosure 20 in which a substantially toroidal cavity 10 is provided, said enclosure being made of metal for example, and said cavity being delimited radially outwardly by two diametrically opposite optical faces that are preferably plane, respectively an inlet face 210 and an outlet face 211, which faces are mutually parallel (to within ±1 minute of angle) and have a light beam 53 passing therethrough (cf. also FIG. 3), and the cavity is delimited radially inwardly by a deformable surface 23 of optical quality. The refractive indices of the faces 210 and 211 and of the deformable surface 23 are close (or substantially equal to) the refractive index of the outside surface of the preform 1 that is to be analyzed. For silica preforms, it is preferable for the faces 210 and 211 to be made of silica and for the deformable surface 23 to be made of silicone. The cavity is filled with a deformable material 22 that is optically uniform and that has a refractive index that is close (or substantially equal) to the index of the elements 210, 211, and 23. Continuity is thus practically achieved, i.e. the refractive index of the medium surrounding the cylindrical preform 1 is isotropic relative to the index of the envelope thereof. The deformable material 22 may be aliphatic hydrocarbon hydrogenated terphenyl (registered trademark), for example.

In practice and as shown in FIG. 1, the enclosure 20 of the index continuity cell 100 is designed to be placed around the cylindrical preform 1 by virtue of an axial opening 27 giving a substantially toroidal configuration to the enclosure 20. Because of the deformable wall 23, a relatively large amount of clearance may be provided between said wall and the outside surface of the preform, thereby making it possible to apply the apparatus of the invention to preforms having diameters lying in a relatively wide range of values. It is thus possible to use a smaller number of index continuity cells than has been possible in the past, or even a single cell. Naturally, the clearance is filled when the index isotropy medium 22 is injected under pressure into the transparent deformable wall 23 which may be constituted, in particular, by a fluid-tight resilient membrane made of silicone (as mentioned above) when the index isotropy medium 22 is a liquid as in the example given above. Contact of the membrane 23 against the preform may be limited to a peripheral annular zone of the preform that corresponds to the optical measurement zone 212 situated on the path of the beam 53. Stable and centered retention relative to the longitudinal axis A of the preform 1 is achieved by locking means constituted by collars 30 and by sealing rings 31, thus making the assembly secure and ensuring that the axis A of the cylindrical preform 1 is parallel with the inlet and outlet planes of the inlet and outlet faces 210 and 211. References 32 and 33 relate to two sealed support rings for the membrane 23 pressing it against two internal shoulders of the annular enclosure 20 of the index continuity cell 100.

Index continuity between the inlet and outlet faces 210 and 211 is thus ensured by contact under pressure between the outside face of the membrane 23 (outside relative to the cavity 10) and the outside surface of the preform 1, thereby expelling any air between said membrane and the preform.

The deformable material 22 is inserted through an injection orifice 24 by injection means (not shown in FIG. 1, but represented diagrammatically in FIG. 2 under reference 25) and at sufficient pressure to ensure that contact is achieved at least over an area of a few mm$^2$ of the deformable wall 23 and the optical measurement zone 212 of the preform 1.

Figure 2:
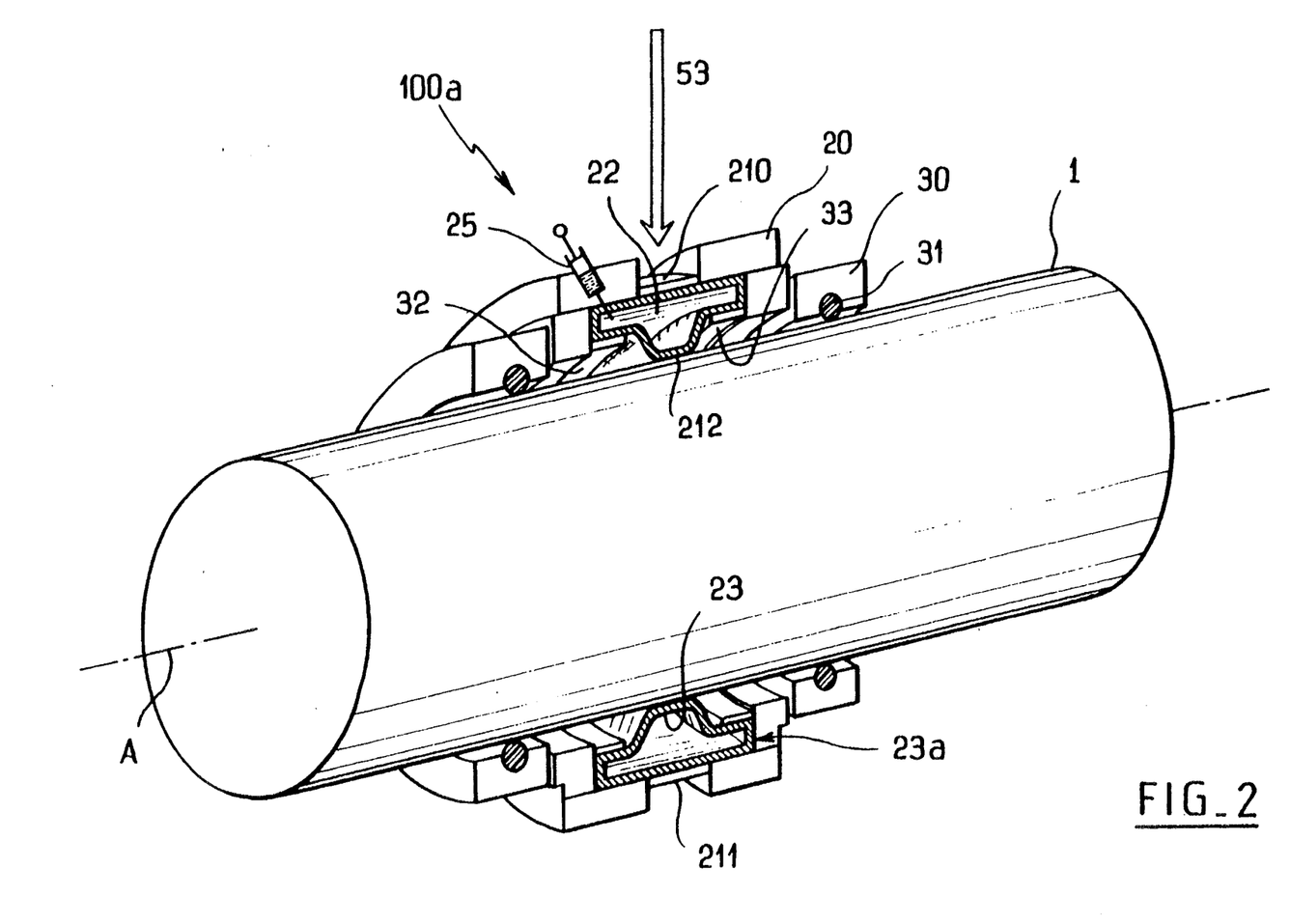
FIG. 2 shows a preferred variant of the embodiment shown in FIG. 1.

FIG. 2 shows a variant embodiment 100a of the index continuity cell that differs from the cell 100 of FIG. 1 in that the deformable surface forming a separation optical interface between the index isotropy medium 22 and the outside surface of the preform 1 is constituted by the inside of a resilient and fluid-tight chamber 23a that is somewhat similar to the inner tube of a pneumatic tire, and which takes up a substantially toroidal configuration under the effect of the index isotropy medium 22 being injected under pressure into said tube. This variant has the advantage of improving sealing of the apparatus.

Figure 3:
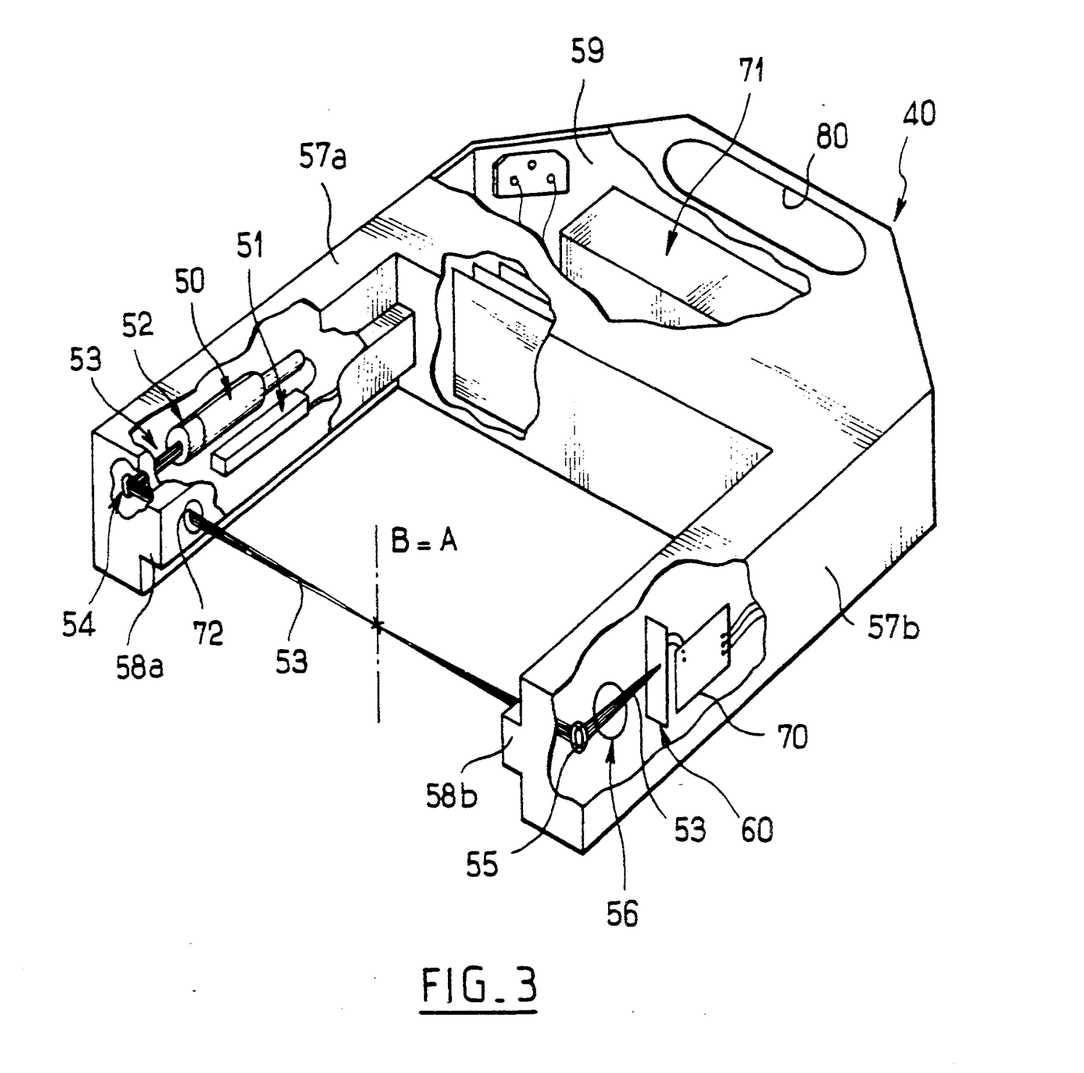
FIG. 3 is a partially cut away diagrammatic perspective view of an embodiment of a measurement cell of the invention.

The index continuity cell 100 or 100a is provided with mechanical guidance and location means suitable for receiving the means required for performing optical measurements, for acquiring the deflection angle, and for calculating the index profile of the preform, with Figure 3 et seq showing one possible embodiment thereof.

These guidance means seek to ensure that the direction of the light beam 53 is orthogonal to the optical inlet and outlet faces 210 and 211 of the index continuity cell 100 or 100a. These means may be implemented mechanically by conventional guidance means provided in the measurement cell 40 and on the index continuity cell 100 or 100a. The mechanical guidance planes are preferably referenced relative both to the optical faces 210 and 211 and to rails 58a and 58b which are described below.

Figure 4:
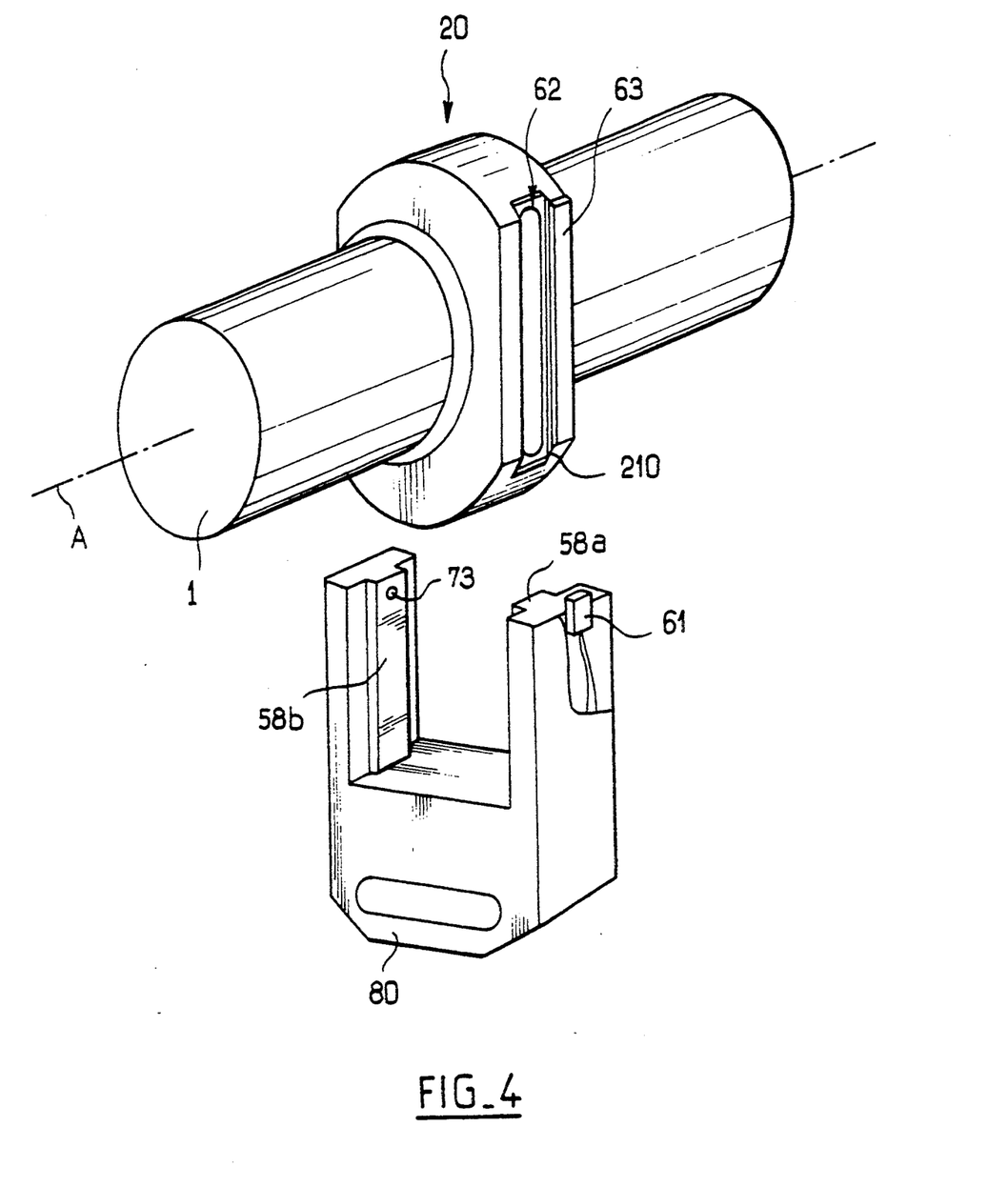
FIG. 4 is a fragmentary perspective diagram of an embodiment of a magnetic device for determining position.

More precisely, FIG. 3 shows an embodiment of the measurement cell 40 implemented in accordance with the present invention and having a horseshoe shape; this cell 40 comprises:

means suitable for emitting a light beam 53 and comprising, in this example, a semiconductor laser 50 (a diode), emitting at 632 nm and associated with a power supply 51, together with a collimator 52 for the light beam 53 and serving to position the waist of the beam 53 (i.e. the narrowest portion of the laser beam 53 which has a size of about 10 μm) on the axis B that coincides approximately with the longitudinal axis A of the preform 1;

optical reflector means 54 and 55, e.g. optical mirrors, each of area not less than the area of the corresponding section of the light beam 53, said beam passing through the two opposite arms of the measurement cell 40 via two windows 72 and 73 (cf. FIG. 3 and FIG. 4);

optical means 56, such as a lens, for focusing the light beam 53;

measurement means 60 such as a photodetection cell of height 30 mm and of width 5 mm, for example, and sensitive to the wavelength of the beam 53, said beam being focused thereon, and the cell delivering an electrical signal proportion to the position of the cell that is illuminated by the beam 53 as focused by the optical means 56 and relative to an origin position, with this applying for each point of incidence of the light beam 53 on the preform 1;

signal acquisition and processing means 70 such as a microprocessor card provided with a signal acquisition card; and power supply means 71 such as a set of rechargeable batteries, enabling the device to operate for a period of at least 1 hour.

The means 50 to 52 and 54 are integrated in one arm 57a of the horseshoe-shaped cell 40, while the means 55, 56, 60, and 70 are integrated in the other arm 57b thereof. The batteries 71 are integrated in the web 59 interconnecting the two opposite arms 57a and 57b of the measurement cell 40.

In addition to the means given above by way of non-limiting example, other means may also be integrated in the measurement cell 40 for the purpose of performing auxiliary functions such as displaying information, inputting data, or playing back data acquired by the computer interface (said additional means are omitted from the figures in order to simply the drawings).

A handle 80 is formed in the web 59 of the measurement cell 40 to facilitate applying the measurement cell to the index continuity cell. The handle 60 defines a means for driving the measurement cell 40 parallel to the inlet and outlet surfaces 210 and 211 of the index continuity cell, and forms a portion of the means for scanning the preform transversely, in co-operation with two relative sliding rails 58a and 58b provided between the measurement cell 40 and the index continuity cell (100 or 100a), and two rectilinear grooves for guiding the two above-specified rails (with only one of the grooves 62 being visible in FIG. 4). In the example shown in FIG. 4, the rails are formed on the inside faces of the two opposite arms 57a and 57b of the measurement cell 40 and the two grooves 62 are formed on the outside of the index continuity cell 100 or 100a. Naturally, the two grooves are centered relative to the inlet and outlet optical surfaces 210 and 211, which surfaces are located at the bottoms of corresponding ones of the grooves. Nevertheless, it is clear that the disposition of the rails and grooves could be inverted. In any event, it is possible to use the handle 80 to slide the measurement cell 40 relative to the index continuity cell 100 or 100a, and to cause it to advance progressively by using position-determining means that are described below.

In practice, optical alignment is obtained by approximately adjusting the angle at which the mirrors 54 and 55 reflect the beam 53 so that the beam 53 passes through the optical axis of the lens 56 and coincides approximately with the center of the detection cell 60. The processor means 70 provide automatic compensation for error in the optical adjustment which gives rise to the detector 60 delivering a signal that is not equal to zero volts.

In order to limit the adjustment-disturbing effects of variations in temperature, vibration, etc., the optical means 50 to 56 and the detection cell 60 as integrated in the two arms 57a and 57b of the measurement cell 50 are advantageously secured to the two arms 57a and 57b which are made of a material having a low drift coefficient, e.g. alumina or silica.

In addition, prior to performing measurement, an operator initializes the measurement electronics. The measurement cell 40 is placed astride the toroidal enclosure 20 of the index continuity cell 100 or 100a, which is disposed around the preform 1 and is held in place by the clamping means 30 and 31. The light beam 53 scans the preform 1 by describing reciprocating motion measured by the above-mentioned position-determining means 63, with the light beam 53 passing right through the preform. A deflection angle is thus acquired.

One embodiment of the means for determining the position of the incident light beam 53 relative to the index continuity cell 100 or 100a comprises a magnetic strip 63 secured to the enclosure 20, e.g. by means of adhesive.

The magnetic strip 63 is preferably aligned with the optical inlet face 210 and is of sufficient length to cover an entire measurement range corresponding to the diameter of the preform 1. The strip 63 has magnetic pole reversals at a pitch d, and a second detection cell 61 responsive thereto, e.g. a Hall effect cell, is connected to the electronics 70, so by counting the number of field reversals the relative position of the light beam 53 is obtained with an accuracy of ±d/2.

The cell 61 is advantageously secured to one of the opposite arms 57a or 57b of the measurement cell 40, in order to provide a measurement reference relative to the reference plane of the cell 40.

A particular advantage of this embodiment lies firstly in the way relative position is measured without making contact and secondly in the way the measurement pitch d is accurately known.

The measurement pitch d is selected as a function of the waist diameter of the light beam 53. In practice, and by way of example, if waist diameter is about 10 μm, then the measurement pitch d should be of the order of 5 μm at a minimum and of 10 μm at a maximum.

By measuring position, it is possible to avoid any need for the reciprocating motion of the measurement cell 40 during measurement to take place at uniform speed, since by acquiring relative position and deflection angle simultaneously, correspondence is achieved automatically.

Figure 5:
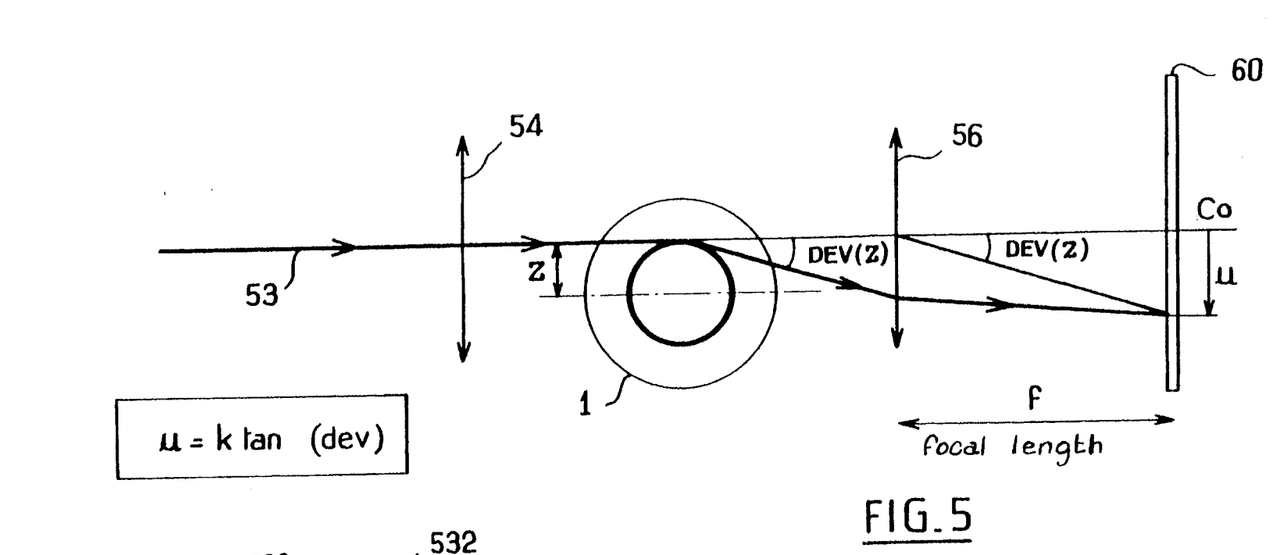
FIG. 5 shows the theory whereby deflection angle is measured.

With reference to FIG. 5, there can be seen a diagram showing how the deflection angle (written "dev") of the light beam 53 passing through the preform 1 is measured. The device comprises inlet optics 54, outlet optics 56, and a detection cell 60 that is sensitive to the wavelength of the light beam 53, that delivers an electrical signal, and that is located at the focus of the lens 56.

The detection cell 60 is positioned so that in the absence of the index continuity cell 100 or 100a, the electrical signal due to illumination by the light beam 53 is zero or comparable to electronic noise.

In the presence of the optical continuity cell 100 or 100a disposed around the preform 1, the detection cell 60 delivers an electrical signal that is proportional to the value u corresponding to the distance between the position of the optical axis B and the position of the light spot on the cell 60. The value u is related to the deflection angle by the following equation:

$$u = k \tan(\text{dev})$$

where k is a constant and can easily be determined from a known deflection "dev".

In the practical embodiment, the optical systems comprising the means 54 and 56, and the cell 60, are all advantageously secured to and thus in positions referred to the opposite arms 57a and 57b of the measurement cell 40, thereby ensuring that the assembly is rigid. By way of example, the inlet lens 54 may have a focal length of 60 mm and a diameter of 10 mm, while the outlet lens 56 has a focal length of 60 mm and a diameter likewise of 60 mm.

Figure 6:
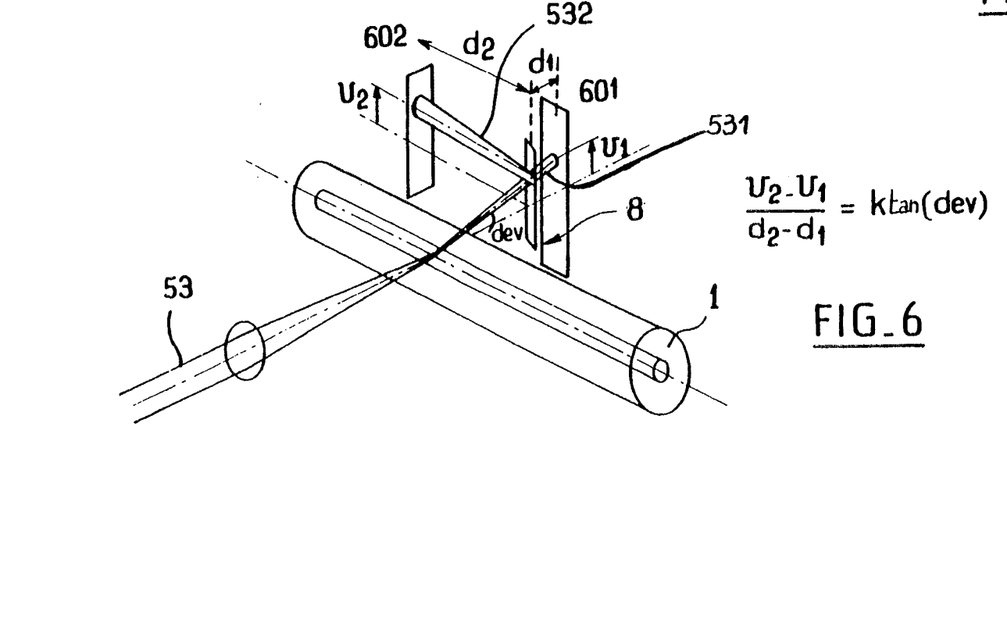
FIG. 6 shows a variant concerning the measurement of deflection angle.

Another implementation of the measurement of the deflection angle "dev" is shown in FIG. 6, where the solution adopted requires two detection cells 601 and 602 both of the same type as the cell 60 in FIG. 5, for example, together with a semireflecting plate 8 (where the elements 601, 602 and 8 are advantageously secured to one of the opposite arms of the measurement cell 40). The optical arrangement is as follows: the light beam 53 is split into two light beams 531 and 532 by the semireflecting plate 8. The beam 531 illuminates the cell 601 while the beam 532 illuminates the cell 602. In the absence of an index continuity cell 100 or 100a surrounding the preform 1, the axes of the light beams 531 and 532 coincide respectively and approximately with the positions on the detection cells 601 and 602 in which the resulting voltages $U_1$ and $U_2$ are zero or of the same order as electronic noise. Electronic processing of the difference $(U_1 - U_2)$ serves to ensure that the value of the measured deflection angle is zero. The deflection "dev" obtained by interposing the index continuity cell surrounding the preform 1 and corresponding to a given relative disposition is obtained from the following equation:

$$(U_2 - U_1)/(d_2 - d_1) = k \tan(\text{dev})$$

where $d_1$ and $d_2$ are the respective distances between the semireflecting plate 8 and each of the measurement cells 601 and 602; and k is a constant that can easily be determined using a known deflection "dev".

In a practical embodiment, the semireflecting plate 8 is 10 mm wide, 50 mm height, and 1 mm thick, for example. The sensitive cells 601 and 602 may be of the type sold by Sitek (registered trademark), for example.

Figure 7:
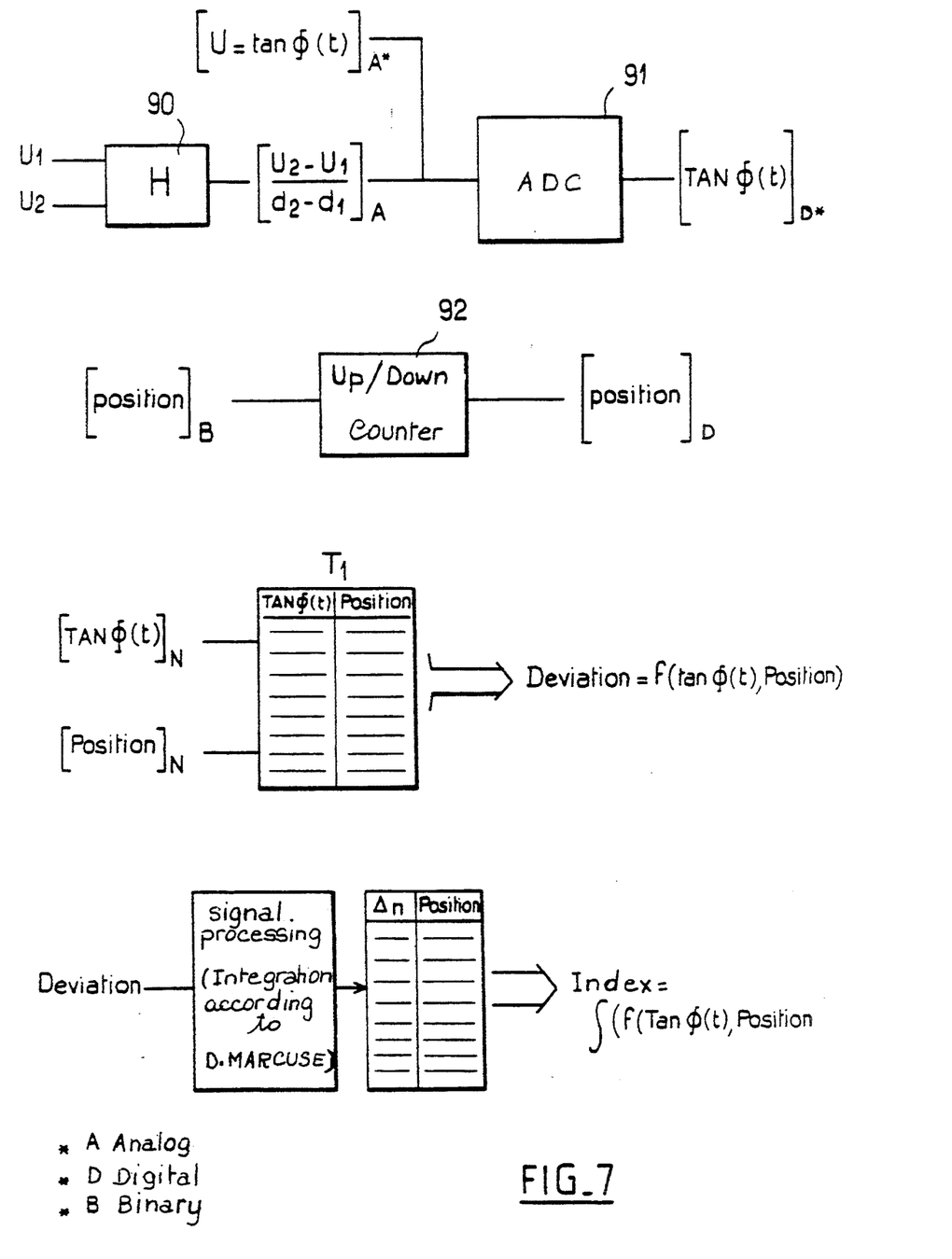
FIG. 7 is a set of block diagrams showing the theory of the signal processing adopted in the context of the present invention.

Reference is now made to FIG. 7 which shows one way of processing the electrical signals delivered by the optical detection cells 601 and 602 and by the magnetic detection cell 60 for detecting the position of the incident light beam 53 relative to the preform 1.

Analog processing means 90 receive the above-mentioned voltages $U_1$ ad $U_2$ as inputs, said voltages being associated with a measurement position z, and it delivers an output voltage proportional to the tangent of the corresponding deflection angle. An analog-to-digital converter ADC 91, e.g. a 12-bit converter, serves to obtain that value in digital form.

Simultaneously, the relative position is also obtained in digital form by an up/down counter 92, e.g. a 16-bit counter, which receives an increment pulse or a decrement pulse for each measurement step (respectively for forwards or reverse motion of the handle).

The digital values corresponding to deflection and to position are stored in the form of a two-dimensional table, thereby associating any given position with a corresponding deflection.

This data table is processed by the microprocessor card, for example (not shown in FIG. 7).

When making approximations to rays that are paraxial, it is well known that index variation $\Delta n$ relative to the index n of the outer layer corresponding to the radius a of the preform is related to the deflection angle by the equation:

$$\Delta n = \frac{1}{\pi} \int_r^a \frac{\tan[\text{dev}(z)]}{\sqrt{(z^2 - r^2)}} dz$$

where r is the radius of the probed index layer (i.e. of the preform) and a is the outside diameter of the preform under investigation. By performing numerical integration, it is possible to obtain a two-dimensional table of points relative any given position z to an index variation $\Delta n(z)$.

We claim:

1. Apparatus for measuring the index profile of an optical fiber preform comprising an outer envelope and a core, the apparatus comprising:
   preform support means;
   emission means for emitting a light beam that is to scan a cross-section of the preform along a diameter thereof;
   an index continuity cell comprising an enclosure provided with a through opening, and serving to press the enclosure around a peripheral annular zone of the preform, together with a cavity formed inside the enclosure so as to surround the above-specified envelope and so as to be in optical communication therewith;
   a medium that is deformable and transparent for the light beam being contained inside the cavity of the enclosure and providing optical index continuity around the preform and relative to the index of the envelope thereof, this being done by passing through a first optical surface constituting an inlet surface for the light beam that scans the preform diametrically, through said medium, and through a second optical surface which constitutes an outlet surface for the light beam, the inlet and outlet first and second optical surfaces being provided in the enclosure transversely relative to the longitudinal axis of the preform, their transverse size being at least equal to the diameter of the preform;
   scanning means for diametrically scanning the light beam across the cross-section of the preform along the diameter thereof;

position determining means for determining the position of the incident light beam on the preform relative to the index continuity cell;

receiver and measurement means for receiving the light beam transmitted through the preform, together with deflection, relative to each incidence point of the emitted beam, said receiver and measurement means also serving to measure the deflection of the beam transmitted through the preform relative to each incidence point, and delivering a signal that is a function of said deflection;

means for processing each of the signals delivered by the receiver and measurement means and also for calculating the variation in the index of the preform along a diameter of its cross-section relative to the index of said medium, with this being done on the basis of a set of measurements of deflection;

wherein said apparatus further comprises a deformable and transparent separation interface between the deformable index continuity medium and the outside surface of the envelope of the preform, said interface serving to adapt the deformable index continuity medium to the outside surface of the envelope of the preform at least over an angular zone thereof, which zone corresponds to an optical measurement zone situated on the path of the light beam, said deformable and transparent interface, and said inlet and outlet optical surfaces for the light beam having a refractive index close to the index of said medium.

2. Apparatus according to claim 1, wherein the index continuity medium is constituted by a liquid or viscous transparent substance, wherein the deformable and transparent interface is constituted by a resilient and impermeable membrane, and wherein the apparatus also includes injection means for injecting the substance into the cavity of the enclosure of the index continuity cell.

3. Apparatus according to claim 2, wherein the resilient and impermeable membrane is extended from each of its transverse annular edges relative to the longitudinal axis of the preform firstly radially outwardly and second longitudinally inwardly from the optical measurement zone so as to define a substantially toroidal fluid-tight continuous chamber designed to be received in the cavity of the enclosure and to be filled with the above-mentioned transparent substance.

4. Apparatus according to claim 1, wherein at least the emission means and the receiver and measurement means, in association with the scanning means for diametrically scanning the cross-section of the preform and also with the above-mentioned calculating and processing means are integrated in a unitary assembly constituting a measurement cell, which is substantially in the form of a horseshoe and is designed to co-operate with the enclosure surrounding the preform and containing the index continuity medium for the purpose of determining the index profile of said preform, the emission means being disposed inside a first arm of the horseshoe-shaped measurement cell while the receiver and measurement means are disposed in the second arm thereof opposite to the first, the first and second arms respectively including a first window for passing the beam emitted by the first arm, and a second window for passing the beam received by the second arm.

5. Apparatus according to claim 4, wherein the scanning means for scanning the preform transversely comprises:

two relative slide rails between the measurement cell and the index continuity cell, extending transversely relative to the longitudinal axis of the preform;

two transverse guide grooves for the two relative slide rails; and drive means for driving the measurement cell parallel to the inlet and outlet surfaces of the index continuity cell.

6. Apparatus according to claim 5, wherein:

the two relative slide rails between the measurement cell and the index continuity cell are provided on the two inside faces of the two opposite arms of the horseshoe-shaped measurement cell; and the two guide grooves for said two relative slide rails are formed in two sides of the index continuity cell, which sides extend transversely relative to the longitudinal axis of the preform and correspond respectively to the inlet and outlet surfaces for the light beam for transversely scanning the preform, said inlet and outlet surfaces occupying the bottoms of the guide grooves.

7. Apparatus according to claim 5, wherein:

the two relative slide rails between the measurement cell and the index continuity cell are provided on two sides of the index continuity cell, which sides extend transversely relative to the longitudinal axis of the preform and correspond to the inlet and outlet surfaces for the light beam for transversely scanning the preform, said inlet and outlet surfaces occupying the radially outermost sides of the two rails; and the two guide grooves for the two relative slide rails are provided in the inside faces of the two opposite arms of the horseshoe-shaped measurement cell.

8. Apparatus according to claim 6, wherein the drive means for driving the measurement cell comprise a handle formed in the web linking together the two opposite arms of said horseshoe-shaped measurement cell, said handle being designed to enable an operator to cause the measurement cell to slide progressively transversely relative to the longitudinal axis of the preform and parallel to the inlet and outlet surfaces of the index continuity cell, with this being done with the assistance of position determining means for determining the position of the incident light beam on the preform.

9. Apparatus according to claim 6, wherein the drive means for driving the measurement cell comprise two stepper motors for two driving racks each disposed on the axially outer sides of each relative slide rail, together with housings distributed along the opposite axially inner walls of each transverse guide groove for a corresponding rail and designed to receive the teeth of the corresponding rack as the rack advances.

10. Apparatus according to claim 4, wherein the measurement cell also has integrated therein display means and/or data input means and/or means for playing back data from the computer interface.

11. Apparatus according to claim 1, wherein the means for determining the position of the incident light beam on the preform comprise a magnetic strip secured to the index continuity cell in alignment with the transverse dimension of the inlet surface of the beam.

12. Apparatus according to claim 1, wherein the index continuity cell co-operates with means for holding said cell in position relative to the measurement zone localized on the preform.

13. Apparatus according to claim 12, wherein the means for holding the index continuity cell in position comprise two lateral clamping collars disposed on either side of said cell and fitted with respective sealing rings, in particular rings made of elastomer, each received in an annular groove formed in the inside wall of the associated collar, each sealing ring serving to apply clamping force from the corresponding collar to the preform, thereby maintaining the index continuity cell in position relative to said preform.

14. Apparatus for measuring the index profile of an optical fiber preform comprising an outer envelope and a core, the apparatus comprising:
preform support means;
emission means for emitting a light beam that is to scan a cross-section of the preform along a diameter thereof;
an index continuity cell comprising an enclosure provided with a through opening, and serving to press the enclosure around a peripheral annular zone of the preform, together with a cavity formed inside the enclosure so as to surround the above-specified envelope and so as to be in optical communication therewith;
a medium that is deformable and transparent for the light beam being contained inside the cavity of the enclosure and providing optical index continuity, around the preform and relative to the index of the envelope thereof, this being done by passing through a first optical surface constituting an inlet surface for the light beam that scans the preform diametrically, through said medium and through a second optical surface which constitutes an outlet surface for the light beam, the inlet and outlet first and second optical surfaces being provided in the enclosure transversely relative to the longitudinal axis of the preform, their transverse size being at least equal to the diameter of the preform;
scanning means for diametrically scanning the light beam across the cross-section of the preform along the diameter thereof;
position determining means for determining the position of the incident light beam on the preform relative to the index continuity cell;
receiver and measurement means for receiving the light beam transmitted through the preform, together with deflection relative to each incidence point of the emitted beam, said receiver and measurement means also serving to measure the deflection of the beam transmitted through the preform relative to each incidence point, and delivering a signal that is a function of said deflection;
means for processing each of the signals delivered by the receiver and measurement means and also for calculating the variation in the index of the preform along a diameter of its
cross section relative to the index of said medium with this being done on the basis of a set of measurements of deflection;
wherein said apparatus comprises further a deformable and transparent separation interface between the deformable index continuity medium and the outside surface of the envelope of the preform, said interface serving to adapt the deformable index continuity medium to the outside surface of the envelope of the preform at least over an angular zone thereof, which zone corresponds to an optical measurement zone situated on the path of the light beam, said deformable and transparent interface, and said inlet and outlet optical surfaces for the light beam having a refractive index close to the index of said medium, and
wherein the index continuity medium is constituted by a liquid or viscous transparent substance, wherein the deformable and transparent interface is constituted by a resilient and impermeable membrane, and wherein the apparatus also includes injection means for injecting the substance into the cavity of the enclosure of the index continuity cell.

15. Apparatus according to clam 14, wherein the resilient and impermeable membrane is extended from each of its transverse annular edges relative to the longitudinal axis of the preform firstly radially outwardly and secondly longitudinally inwardly from the optical measurement zone so as to define a substantially toroidal fluid-tight continuous chamber designed to be received in the cavity of the enclosure and to be filled with the abovementioned transparent substance 16. Apparatus according to claim 14, wherein at least the emission means and the receiver and measurement means, in association with the scanning means for diametrically scanning the cross-section of the preform and also with the above-mentioned calculating and processing means are integrated in a unitary assembly constituting a measurement cell, which is substantially in the form of a horseshoe and is designed to cooperate with the enclosure surrounding the preform and containing the index continuity medium for the purpose of determining the index profile of said preform, the emission means being disposed inside a first arm of the horseshoe-shaped measurement cell while the receiver and measurement means are disposed in the second arm thereof opposite to the first, the first and second arms respectively including a first window for passing the beam emitted by the first arm, and a second window for passing the beam received by the second arm.

17. Apparatus according to claim 16, wherein the scanning means for scanning the preform transversely comprise;
two relative slide rails between the measurement cell and the index continuity cell, extending transversely relative to the longitudinal axis of the preform;
two transverse guide grooves for the two relative slide rails; and
drive means for driving the measurement cell parallel to the inlet and outlet surfaces of the index continuity cell.

18. Apparatus according to claim 17, wherein;
the two relative slide rails between the measurement cell and the index continuity cell are provided on the two inside faces of the two opposite arms of the horseshoe-shaped measurement cell; and
the two guide grooves for said two relative slide rails are formed in two sides of the index continuity cell, which sides extend transversely relative to the longitudinal axis of the preform and correspond respectively to the inlet and outlet surfaces for the light beam for transversely scanning the preform, said inlet and outlet surfaces occupying the bottoms of the guide grooves.

19. Apparatus according to claim 17, wherein;
the two relative slide rails between the measurement cell and the index continuity cell are provided on two sides of the index continuity cell, which sides extend transversely relative to the longitudinal axis of the preform and correspond to the inlet and outlet surfaces for the light beam for transversely scanning the preform, said inlet and outlet surfaces occupying the radially outermost sides of the two rails; and the two guide grooves for the two relative side rails are provided in the inside faces of the two opposite arms of the horseshoe-shaped measurement cell.

20. Apparatus according to claim 18, wherein the drive means for driving the measurement cell comprise a handle formed in the web linking together the two opposite arms of said horseshoe-shaped measurement cell, said handle being designed to enable an operator to cause the measurement cell to slide progressively transversely relative to the longitudinal axis of the preform and parallel to the inlet and outlet surfaces of the index continuity cell, with this being done with the assistance of position determining means for determining the position of the incident light beam on the preform.

21. Apparatus according to claim 18, wherein the drive means for driving the measurement cell comprise two stepper motors for two driving racks each disposed on the axially outer sides of each relative slide rail, together with housings distributed along the opposite axially inner walls of each transverse guide groove for a corresponding roll and designed to receive the teeth of the corresponding rack as the rack advances.

22. Apparatus according to claim 16, wherein the measurement cell also has integrated therein display means and/or data input means and/or means for playing back data from the computer interface.

23. Apparatus according to claim 14, wherein the means for determining the position of the incident light beam on the preform comprise a magnetic strip secured to the index continuity cell in alignment with the transverse dimension of the inlet surface of the beam.

24. Apparatus according to claim 14, wherein the index continuity cell cooperates with means for holding said cell in position relative to the measurement zone localized on the preform.

25. Apparatus according to claim 24, wherein the means for holding the index continuity cell in position comprise two lateral clamping collars disposed on either side of said cell and fitted with respective sealing rings, in particular rings made of elastomer, each received in an annular groove formed in the inside wall of the associated collar, each sealing ring serving to apply clamping force from the corresponding collar to the preform, thereby maintaining the index continuity cell in position relative to said preform.

26. Apparatus for measuring the index profile of an optical fiber preform comprising an outer envelope and a core, the apparatus comprising:

preform support means;

emission means for emitting a light beam that is to scan a cross-section of the preform along a diameter thereof;

an index continuity cell comprising an enclosure provided with a through opening, and serving to press the enclosure around a peripheral annular zone of the preform, together with a cavity formed inside the enclosure so as to surround the above-specified envelope and so as to be in optical communication therewith;

a medium that is deformable and transparent for the light beam being contained inside the cavity of the enclosure and providing optical index continuity, around the preform and relative to the index of the envelope thereof, this being done by passing through a first optical surface constituting an inlet surface for the light beam that scans the preform diametrically, through said medium, and through a second optical surface which constitutes an outlet surface for the light beam, the inlet and outlet first and second optical surfaces being provided in the enclosure transversely relative to the longitudinal axis of the preform, their transverse size being at least equal to the diameter of the preform;

scanning means for diametrically scanning the light beam across the cross-section of the preform along the diameter thereof;

position determining means for determining the position of the incident light beam on the preform relative to the index continuity cell;

receiver and measurement means for receiving the light beam transmitted through the preform, together with deflection, relative to each incidence point of the emitted beam, said receiver and measurement means also serving to measure the deflection of the beam transmitted through the preform relative to each incidence point, and delivering a signal that is a function of said deflection;

means for processing each of the signals delivered by the receiver and measurement means and also for calculating the variation in the index of the preform along a diameter of its cross-section relative to the index of said medium, with this being done on the basis of a set of measurements of deflection;

wherein said apparatus further comprises a deformable and transparent separation interface between the deformable index continuity medium and the outside surface of the envelope of the preform, said interface serving to adapt the deformable index continuity medium to the outside surface of the envelope of the preform at least over an angular zone thereof, which zone corresponds to an optical measurement zone situated on the path of the light beam, said deformable and transparent interface, and said inlet and outlet optical surfaces for the light beam having a refractive index close to the index of said medium, and wherein at least the emission means and the receiver and measurement means, in association with the scanning means for diametrically scanning the cross-section of the preform and also with the above-mentioned calculating and processing means are integrated in a unitary assembly constituting a measurement cell, which is substantially in the form of a horseshoe and is designed to cooperate with the enclosure surrounding the preform and containing the index continuity medium for the purpose of determining the index profile of said preform, the emission means being disposed inside a first arm of the horseshoe-shaped measurement cell while the receiver and measurement means are disposed in the second arm thereof opposite to the first, the first and second arms respectively including a first window for passing the beam emitted by the first arm, and a second window for passing the beam received by the second arm.

27. Apparatus according to claim 26, wherein the index continuity medium is constituted by a liquid or viscous transparent substance, wherein the deformable and transparent interface is constituted by a resilient and impermeable membrane, and wherein the apparatus also includes injection means for injecting the substance into the cavity of the enclosure of the index continuity cell.

28. Apparatus according to claim 27, wherein the resilient and impermeable membrane is extended from each of its transverse annular edges relative to the longitudinal axis of the preform firstly radially outwardly and secondly longitudinally inwardly from the optical measurement zone so as to define a substantially toroldal fluid-tight continuous chamber designed to be received in the cavity of the enclosure and to be filled with the abovementioned transparent substance.

29. Apparatus according to claim 26, wherein the scanning means for scanning the preform transversely comprise;
two relative slide rails between the measurement cell and the index continuity cell, extending transversely relative to the longitudinal axis of the preform;
two transverse guide grooves for the two relative slide rails; and
drive means for driving the measurement cell parallel to the inlet and outlet surfaces of the index continuity cell.

30. Apparatus according to claim 29, wherein;
the two relative slide rails between the measurement cell and the index continuity cell are provided on the two inside faces of the two opposite arms of the horseshoe-shaped measurement cell; and
the two guide grooves for said two relative slide rails are formed in two sides of the index continuity cell, which sides extend transversely relative to the longitudinal axis of the preform and correspond respectively to the inlet and outlet surfaces for the light beam for transversely scanning the preform, said inlet and outlet surfaces occupying the bottoms of the guide grooves.

31. Apparatus according to claim 29, wherein
the two relative slide rails between the measurement cell and the index continuity cell are provided on two sides of the index continuity cell, which sides extend transversely relative to the longitudinal axis of the preform and correspond to the inlet and outlet surfaces for the light beam for transversely scanning the preform, said inlet and outlet surfaces occupying the radially outermost sides of the two rails; and
the two guide grooves for the two relative slide rails are provided in the inside faces of the two opposite arms of the horseshoe-shaped measurement cell.

32. Apparatus according to claim 30, wherein the drive means for driving the measurement cell comprise a handle formed in the web linking together the two opposite arms of said horseshoe-shaped measurement cell, said handle being designed to enable an operator to cause the measurement cell to slide progressively transversely relative to the longitudinal axis of the preform and parallel to the inlet and outlet surfaces of the index continuity cell, with this being done with the assistance of position determining means for determining the position of the incident light beam on the preform.

33. Apparatus according to claim 30, wherein the drive means for driving the measurement cell comprise two stepper motors for two driving racks each disposed on the axially outer sides of each relative slide rail, together with housings distributed along the opposite axially inner walls of each transverse guide groove for a corresponding rail and designed to receive the teeth of the corresponding rack as the rack advances.

34. Apparatus according to claim 26, wherein the measurement cell also has integrated therein display means and/or data input means and/or means for playing back data from the computer interface.

35. Apparatus according to claim 26, wherein the means for determining the position of the incident light beam on the preform comprise a magnetic strip secured to the index continuity cell in alignment with the transverse dimension of the inlet surface of the beam.

36. Apparatus according to claim 26, wherein the index continuity cell cooperates with means for holding said cell in position relative to the measurement zone localized on the preform.

37. Apparatus according to claim 36, wherein the means for holding the index continuity cell in position comprise two lateral clamping collars disposed on either side of said cell and fitted with respective sealing rings, in particular rings made of elastomer, each received in an annular groove formed in the inside wall of the associated collar, each sealing ring serving to apply clamping force from the corresponding collar to the preform, thereby maintaining the index continuity cell in position relative to said preform.

38. Apparatus for measuring the index profile of an optical fiber preform comprising an outer envelope and a core, the apparatus comprising;
preform support means;
emission means for emitting a light beam that is to scan a cross section of the preform along a diameter thereof;
an index continuity cell comprising an enclosure provided with a through opening, and serving to press the enclosure around a peripheral annular zone of the preform, together with a cavity formed inside the enclosure so as to surround the above-specified envelope and so as to be in optical communication therewith;
a medium that is deformable and transparent for the light beam being contained inside the cavity of the enclosure and providing optical index continuity, around the preform and relative to the index of the envelope thereof, this being done by passing through a first optical surface constituting an inlet surface for the light beam that scans the preform diametrically, through said medium, and through a second optical surface which constitutes an outlet surface for the light beam, the inlet and outlet first and second optical surfaces being provided in the enclosure transversely relative to the longitudinal axis of the preform, their transverse size being at least equal to the diameter of the preform;
scanning means for diametrically scanning the light beam across the cross-section of the preform along the diameter thereof;
position determining means for determining the position of the incident light beam on the preform relative to the index continuity cell;
receiver and measurement means for receiving the light beam transmitted through the preform, together with deflection, relative to each incidence point of the emitted beam, said receiver and measurement means also serving to measure the deflection of the beam transmitted through the preform relative to each incidence point, and delivering a signal that is a function of said deflection;
means for processing each of the signals delivered by the receiver and measurement means and also for calculating the variation in the index of the preform along a diameter of its cross-section relative to the index of said medium, with this being done on the basis of a set of measurements of deflection; wherein said apparatus further comprises a deformable and transparent separation interface exists between the deformable index continuity medium and the outside surface of the envelope of the preform, said interface serving to adapt the deformable index continuity medium to the outside surface of the envelope of the preform at least over an angular zone thereof, which zone corresponds to an optical measurement zone situated on the path of the light beam, said deformable and transparent interface, and said inlet and outlet optical surfaces for the light beam having a refractive index close to the index of said medium, and wherein the means for determining the position of the incident light beam on the preform comprise a magnetic strip secured to the index continuity cell in particular by means of adhesive, and in alignment with the transverse dimension of the inlet surface of the beam for performing transverse scanning of the preform.

* * * * *

UNITED STATES PATENT AND TRADEMARK OFFICE
CERTIFICATE OF CORRECTION

PATENT NO. : 5,450,192
DATED : September 12, 1995
INVENTOR(S) : Nolf et al.

It is certified that error appears in the above-indentified patent and that said Letters Patent is hereby corrected as shown below:

Title page, item [54] and column 1, lines 2-6 delete "APPARATUS INCLUDING AN INDEX CONTINUITY CELL FOR MEASURING THE INDEX PROFILE OF AN OPTICAL FIBER PREFORM HAVING AN OUTER ENVELOPE AND A CORE"

insert --APPARATUS INCLUDING AN INDEX CONTINUITY CELL FOR MEASURING THE INDEX PROFILE OF AN OPTICAL FIBER PREFORM--

Signed and Sealed this

Nineteenth Day of March, 1996

Attest:

BRUCE LEHMAN

Attesting Officer

Commissioner of Patents and Trademarks